United States Patent [19]

Pedersen

[11] Patent Number: 5,425,868
[45] Date of Patent: Jun. 20, 1995

[54] SENSOR FOR NON-INVASIVE, IN VIVO DETERMINATION OF AN ANALYTE AND BLOOD FLOW

[75] Inventor: Knud G. Pedersen, Lyngby, Denmark

[73] Assignee: Radiometer A/S, Bronshonj, Denmark

[21] Appl. No.: 97,377

[22] Filed: Jul. 23, 1993

[30] Foreign Application Priority Data

Jul. 24, 1992 [DK] Denmark .............................. 0957/92

[51] Int. Cl.[6] .......................................... G01N 27/404
[52] U.S. Cl. ................................. 204/408; 128/635; 128/637; 128/639; 204/415
[58] Field of Search .................... 204/153.17, 415, 408; 128/639–644, 637, 635

[56] References Cited

U.S. PATENT DOCUMENTS

| | | | |
|---|---|---|---|
| 4,114,602 | 9/1978 | Huch et al. | 128/635 |
| 4,259,963 | 4/1981 | Huch | 128/635 |
| 4,296,752 | 10/1981 | Welsh et al. | 128/635 |
| 4,324,256 | 4/1982 | Vesterager | 204/415 |
| 4,333,473 | 6/1982 | Eberhard et al. | 204/415 |
| 4,539,994 | 9/1985 | Baumbach et al. | 128/635 |
| 4,601,293 | 7/1986 | Foster et al. | 128/635 |
| 5,114,859 | 5/1992 | Kagenow | 204/418 |

FOREIGN PATENT DOCUMENTS

WO83/01510  4/1983  WIPO .

OTHER PUBLICATIONS

Acta anaesth, scand. 1978 month unavailable Suppl. 68, 33–39–"A Transcutaneous Po2 Electrode Incorporating a Thermal Clearance Local Blood Flow Sensor".

Primary Examiner—T. Tung
Attorney, Agent, or Firm—David M. Klein; Bryan Cave

[57] ABSTRACT

The sensor (1) comprises a sensor body (3) thermostatable by means of a first thermostating system (14,15) and having an outer surface (3a,40a) for application to the human body (28) in heat conductive relationship therewith, said outer surface (3a,40a) forming the measuring surface of the sensor (1). The sensor (1) further comprises analyte sensing means (7,8) arranged in said sensor body (3) and being thermostated through said body (3) by means of the first thermostating system (14,15). The sensor (1) further comprises means (16,41) arranged in the sensor body (3) in heat insulated relationship therewith while in heat conductive relationship with a delimited surface part of the sensor measuring surface (3a,40a). The means (16,41) is thermostatable by means of a second thermostating system. The delimited surface part is located within the outer periphery of the sensor measuring surface (3a,40a).

9 Claims, 3 Drawing Sheets

SENSOR FOR NON-INVASIVE, IN VIVO DETERMINATION OF AN ANALYTE AND BLOOD FLOW

The invention relates to a sensor for non-invasive, in vivo determination of an analyte and blood flow comprising a sensor body thermostatable by means of a first thermostating system and having an outer surface for application to the human body in heat conductive relationship therewith, said outer surface forming the measuring surface of the sensor, the sensor further comprising analyte sensing means arranged in said sensor body and being thermostated through said body by means of the first thermostating system, said analyte sensing means having a measuring surface opening into the sensor measuring surface.

In various situations it is advantageous to get a simultaneous non-invasive, in vivo determination of an analyte and blood flow.

It is well-known in the art that transcutaneously (tc) measured values of the $O_2$ content of a patients blood, $p_wO_2$, do not always reflect the arterial values as the transcutaneous values vary dependent on the blood flow in the tissue located beneath the measuring site. In case the arterial values are to be determined from tc values it may thus be necessary to determine the blood flow beneath the measuring site as well.

As the blood flow controls the amount of $O_2$ actually provided to the tissue of a patient and as $p_wO_2$ is an indicator of the $O_2$ uptake in the tissue, it is possible through a simultaneous determination of said parameters to determine whether the $O_2$ supply to the tissue of a patient is hemodynamically controlled, i.e. dependent on disturbances of the blood flow, or is respiratory controlled, i.e. dependent on disturbances of the $O_2$ uptake in the lungs.

In tc measurements of blood gas parameters and blood flow it is necessary to measure at a temperature above the usual body temperature, and thus tc sensors are often adapted to heat the sensor and the measuring site to such a higher temperature. The temperature increase necessary for measuring blood flow is usually a little larger than the temperature increase necessary for measuring blood gases. For example, a well-established measurement of blood flow requires a measuring temperature of approx. 44° C., whereas blood gases may be measured at a temperature of approx. 42° C. However, a temperature increase of the measuring site during a long time may injure the patient. Thus, the time applicable for measuring at one site is reduced. The relationship between the measuring time and the measuring temperature is such that the higher the measuring temperature, the shorter the applicable measuring time. Thus, when simultaneously measuring a blood gas parameter and blood flow it is desirable to measure said values at their respective temperatures without heating the measuring site to the higher temperature.

A sensor for transcutaneously measuring $O_2$ simultaneously with the determination of a blood flow indicator value is disclosed in Parker D et al. A Transcutaneous $P_{O2}$ Electrode Incorporating a Thermal Clearance Local Blood Flow Sensor. Acta Anaesth Scand 1978; S 68: 33–39. The $p_wO_2$ sensor disclosed therein comprises a container shaped anode arranged in a sensor body. The interior of the anode is filled with an epoxy casting wherein a cathode is centrally embedded. A heating element for heating the sensor and the skin to be measured surrounds the anode. The sensor further comprises two temperature sensors in the form of thermistors, one of said thermistors being arranged in the anode, the other being arranged adjacent to the cathode. Prior to measuring on a patient, the entire sensor is heated to the predetermined measuring temperature. During measuring the anode is kept at said temperature by means of the heating element, whereas the cathode is not heated. In this sensor the heated anode provides a heat shield during measuring protecting the cathode against influences due to changes in the temperature of the surroundings. Thus, it is assumed that changes in the temperature of the cathode are caused only by heat dissipation to the skin and tissue beneath the sensor. A value indicative of the blood flow in the tissue beneath the sensor is obtained by measuring the temperatures difference between the two thermistors of the sensor, i.e. the temperature difference between the heated anode and the unheated cathode, during a measurement.

However, the above sensor has a major drawback in that the temperatures of the cathode is not constant during measuring, as said temperature varies with the heat dissipation to the skin and tissue. Further, a temperature gradient is present from the anode through the epoxy layer in the sensor to the cathode, which gradient is not constant due to the variable temperature of the cathode. The size of said temperature gradient is unknown, but is estimated to approx. 1°. Thus, the temperature conditions for measuring $pO_2$ are not well-established. Furthermore, the blood flow is only indirectly determined as the determination is performed by measuring the temperature difference between two different points in the sensor-not by measuring the power actually dissipated in the tissue. The integration of the thermistors for measuring blood flow with the blood gas measuring means results in the blood flow and blood gas measuring means having approximately the same temperature (the temperature necessary for measuring blood flow) during measuring. Thus, it is not possible to measure $p_wO_2$ and blood flow at their respective temperatures by means of this sensor.

A sensor for simultaneously measuring $p_wO_2$, $p_wCO_2$, and the blood flow of the tissue beneath the sensor is disclosed in International Patent Application WO 83/01510. Said sensor comprises a heat conductive substrate arranged at the front of the sensor and temperature controlled by means of a thermostating system comprising a heating element and a temperature sensor. The gas measuring means are arranged in and heated together with the substrate. The substrate is surrounded by, but not in contact with a heat conductive jacket. The temperature or said jacket is controlled by means of a second substrate thermostated by a second thermostating system also comprising a heating element and a temperature sensor. Prior to measuring, the two substrates and the heat jacket are heated to the same temperature. Thus, the jacket forms a protecting heat shield surrounding the substrate located at the measuring front of the sensor, and the heat flux between the substrate and the jacket is zero. During measuring, the jacket and the substrate are kept at the same temperature and thus the heat from the substrate will dissipate into the tissue beneath the sensor. A value indicative of the amount of heat dissipated from the substrate to the tissue beneath the sensor and thus an indication of the blood flow at this site is obtained by measuring the power necessary to keep the substrate at the initial temperature during measuring.

The system for measuring blood flow has a large thermal mass due to the integration of the measuring means and the substrate used for measuring blood flow in the tissue. Accordingly, said system reacts relatively slowly. Further, it is impossible to measure the content of $O_2$ and $CO_2$ at one temperature and blood flow at another temperature, as it is necessary to maintain the entire sensor as well as the measuring site at the temperature appropriate for measuring blood flow. Finally, the design comprising the shielding heat jacket causes the sensor to have an excessively large diameter.

The object of the invention is to provide a sensor for simultaneous measuring an analyte and blood flow overcoming the above drawbacks in a simple manner. This is obtained by the sensor according to the invention which is characteristic in that the sensor further comprises means arranged in the sensor body in heat insulated relationship therewith while in heat conductive relationship with a delimited surface part of the sensor measuring surface and being thermostatable by means of a second thermostating system, and that said delimited surface part is located within the outer periphery of the sensor measuring surface.

The analytes to be measured are for example $O_2$ and $CO_2$ (cf. the sensors mentioned in the introduction). Also other analytes can be determined by means of a sensor according to the invention, such as the analytes stated in the introduction to U.S. Pat. No. 5,114,859, Kagenow H and in Walter B. Construction of Dry Reagent Chemistries; Use of Reagent Immobilization and Compartmentalization Techniques. Methods in Enzymology 1988; 137/Pt D: 411 Table III. The content of said publications is considered incorporated into the present application by reference to the publications.

The analyte determining means may comprise for example electrochemical sensors, optical sensors, or other types of sensors suitable for determination of an analyte by non-invasive, in vivo measuring.

In a preferred embodiment of a sensor according to the invention the analyte sensing means comprise blood gas measuring means.

As the two thermostating systems are independently thermostated they may be thermostated to the same or to their respective temperatures. By means of the sensor according to the invention it is thus possible to measure an analyte and blood flow at their respective temperatures, for example as mentioned above by measuring a blood gas parameter and blood flow at 42° and 44°, respectively. The individual thermostating of the analyte measuring means and the blood flow measuring means further ensures that well-established temperature conditions are obtained in both measurements.

By arranging the delimited surface part within the outer periphery of the sensor measuring surface, the heat flux from the measuring surface surrounding said delimited surface part provides a heat shield in the tissue, said heat shield surrounding the heat flux from the delimited surface part. Thereby the heat flux from the delimited surface part is guided substantially unidirectionally to the tissue located directly beneath the delimited surface part and absorbed therein.

The delimited surface part in the sensor measuring surface may comprise a part of the sensor body proper or may comprise a separate layer. In the former case, the part of the sensor body forming the delimited surface part has to be arranged in heat conductive relationship with the means thermostatable by the second thermostating system, thus essentially being heated by said means and not by the first thermostating system. When the delimited surface part comprises a separate layer applied to the sensor body, it is preferred that the thermostatable means arranged in the sensor body are located in a recess opening into the sensor measuring surface and being covered with a layer of a heat conductive material at said surface, said layer forming said delimited surface part of the sensor measuring surface.

The thermostating systems may each comprise several parts, for example a heating element and a temperature sensor, or comprise one single component constituting both heating element and temperature sensor. In a preferred embodiment of a sensor according to the invention a self-thermostating element forms the thermostatable means arranged in the sensor body and the second thermostating system as well. This embodiment is advantageous in that fewer supply lines to the sensor are required.

In a further preferred embodiment the self-thermostating element comprises a thermistor. In yet a further preferred embodiment the self-thermostating element comprises a resistance wire. Said resistance wire should be made of a material having a well-established temperature characteristic, for example Pt and Ni. The two latter embodiments according to the invention are advantageous in that the self-thermostating element has a small thermal mass, the element thus providing a quick response even to small variations in temperature.

The invention will be further described below with reference to the drawings and the subsequent examples.

BRIEF DESCRIPTION OF THE DRAWINGS

In the various figures like reference numerals are used to denote like parts.

Figure 1:
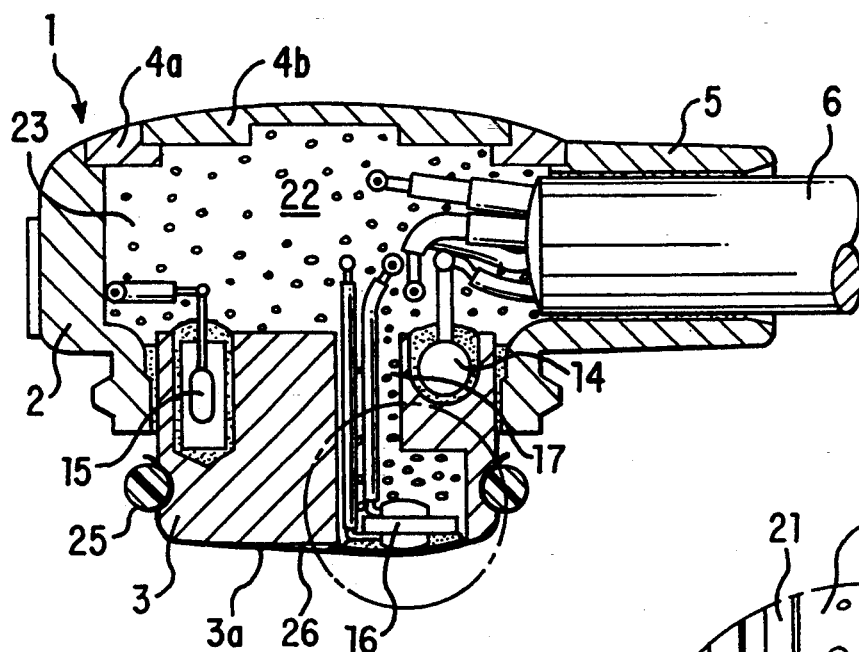
FIG. 1 is a partial cross section of parts of a first embodiment of a sensor according to the invention.
Figure 1A:
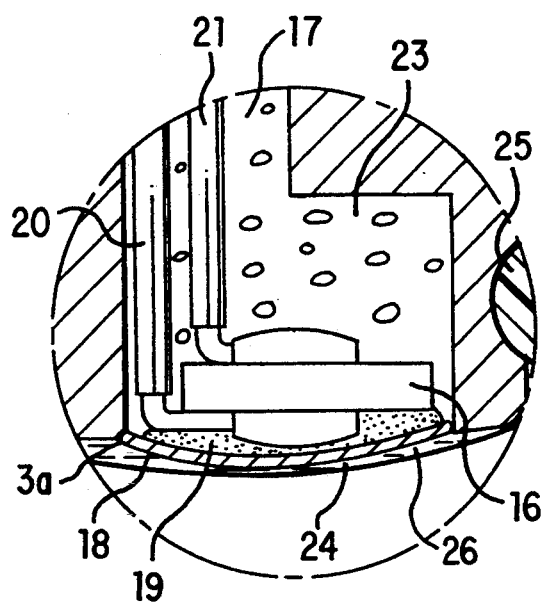
FIG. 1a is a section of FIG. 1 on an enlarged scale.
Figure 2:
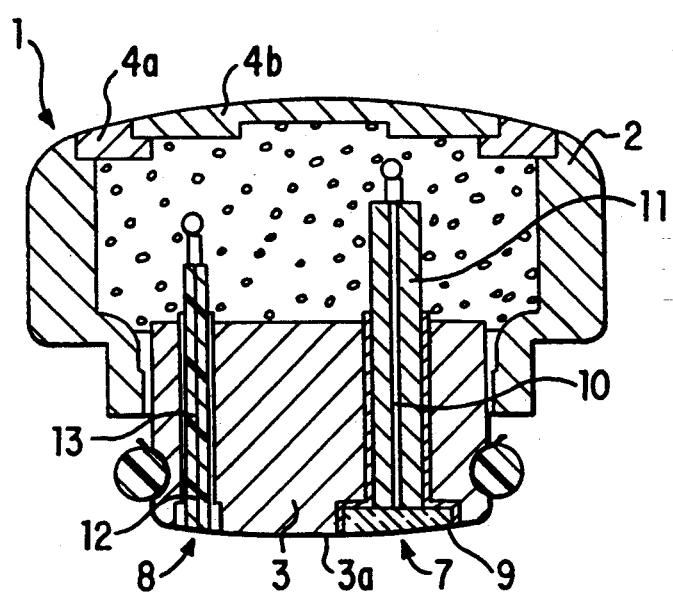
FIG. 2 is a second partial cross section of the sensor shown in FIG. 1.

The embodiment of a sensor according to the invention shown in FIGS. 1, 1a and 2 is a combined sensor 1 for transcutaneous (tc) measurements of $pCO_2$ and $pO_2$. The sensor 1 is configured essentially as existing, well-known tc sensors, for example the combined tc sensor of the type E5280 from Radiometer A/S, Copenhagen, Denmark. The sensor 1 comprises a sensor housing 2 of an electric insulating material, for example polyphenyleneoxide (PPO), into which a sensor body 3 of silver is glued. The sensor housing 2 is closed by two additional housing parts 4a and 4b made of an electric insulating material as well. The sensor 1 is via a cable 6 connected to a not shown monitor controlling the various functions relating to in vivo monitoring, i.a. connecting/disconnecting current circuits, processing data, etc. The interface between the sensor 1 and the cable 6 is reinforced by means of a tubular extension 5 of the housing 2.

A heating element 14 in the form of a Zener diode is embedded in the sensor body 3, said heating element 14 heating the sensor body 3 and the skin measuring site. A temperature sensor 15 in the form or a NTC resistor is also embedded in the sensor body 3. The heating element 14 and the temperature sensor 15 are both glued into the sensor body 3 by means of a heat conductive glue and are connected to the controlling monitor via the cable 6.

Sensor parts 7 and 8 for measuring $PCO_2$ and $pCO_2$, respectively, are arranged in the sensor body 3, the measuring surfaces of said parts 7, 8 opening into an outer surface 3a of the sensor body 3. Said outer surface 3a forms the measuring surface of the sensor 1. The outer surface 3a is chlorinated and the sensor body 3 serves as a reference electrode for the $pCO_2$ measurements and as an anode for the $pO_2$ measurements. The sensor body 3 is also connected to the monitor via the cable 6.

Measuring $pCO_2$ is performed in a well-known manner based on measuring pH. The measurement is performed by means of the $pCO_2$ sensor part 7 comprising a solid state element 9 and a conductive Ag wire 10, the conductive wire 10 connecting the solid state element 9 with the cable 6. The solid state element 9 comprises several layers. The outer layer is a pH sensitive glass layer arranged on a layer of electron-conductive glass which again is arranged on an intermediate conductor of Pt. These layers are carried by an insulating ceramic basis. The conductive glass layer converts the measurement signal from the pH sensitive glass into electric signals and transmits said signals through the intermediate conductor to the conductive wire 10, which is surrounded by an insulating plastic tube 11 in the sensor body 3.

Measuring $O_2$ is performed in a well-known manner as well by applying a polarization voltage across the sensor part 8 (constituting the cathode part) and the sensor body 3 and measuring the resulting current in this circuit. The sensor part 8 comprises a Pt wire 12 casted into a glass element 13 which again is glued into the sensor body 3. The Pt wire is connected to the cable 6 in the sensor housing 2.

The sensor 1 further comprises a thermistor 16 in the form of a NTC resistor (Dale Electronics GmbH, Pucheim, Germany), arranged in a through-going recess 17 in the sensor body 3. The thermistor 16 is connected to cables 20 and 21 which again are connected to the controlling monitor via the cable 6. The thermistor 16 is a self-thermostating unit and thus operates as a heat supplying element as well as a temperature sensor. The part of the recess 17 opening into the sensor measuring surface 3a is covered by a silver calotte 18, the thermistor 16 being glued to the inside of said calotte 18 by means of heat conductive glue 19 of the type Epotek H31 (Epoxy Technology Inc., Billerica, U.S.A.). In this manner a good thermal connection between the thermistor 16 and the calotte part 18 of the sensor measuring surface 3a is ensured.

The recess 17 and the space 22 delimited by the sensor housing 2, the sensor body 3 and the housing parts 4a and 4b, are filled with an epoxy casting 23. Said epoxy insulates the thermistor 16 from the sensor body 3 so that the heat transfer gradient between the thermistor 6 and the sensor body 3 is small. By means of the above-mentioned good thermal connection between the thermistor 16 and the calotte 18 it is then ensured that power dissipated as heat in the thermistor 16 is supplied to the calotte 18 and not to the sensor body 3.

A 15 $\mu$m PP membrane 24 is stretched across the sensor measuring surface 3a, said membrane 24 being secured to the sensor body 3 by means of an O-ring 25. A bicarbonate-containing electrolyte fluid 26 is captured between the sensor measuring surface 3a and the membrane 24.

Figure 3:
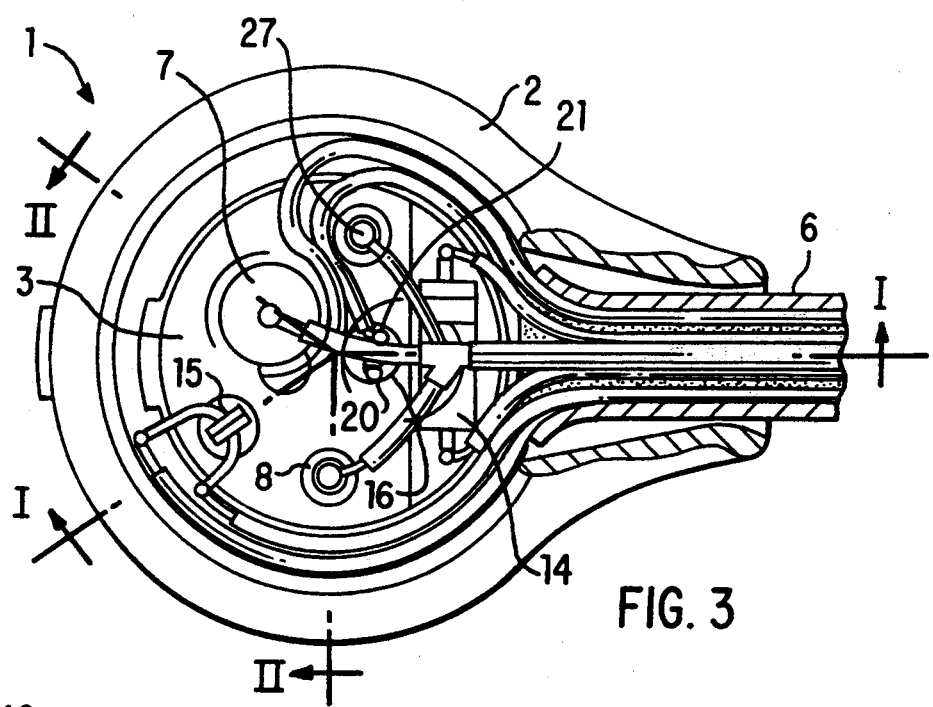
FIG. 3 is a partial cross section of the sensor shown in FIGS. 1 and 2 seen from above.

FIG. 3 is a partial cross section of the sensor 1 seen in FIGS. 1 and 2 shown from above. The housing parts 4a and 4b are removed and the upper part of the cable 6 cut away, exposing the different parts arranged in the sensor body 3, such as the $pCO_2$ sensor part 7, the $pO_2$ sensor part 8, the heating element 14, the temperature sensor 15, and the thermistor 16. Further is shown how said parts are connected to the cable 6. The sensor body 3 proper is also connected to the cable 6 in a contact point 27. The section lines I—I and II—II shown in FIG. 3 corresponds to the cross sections shown in FIGS. 1 and 2, respectively.

Figure 4:
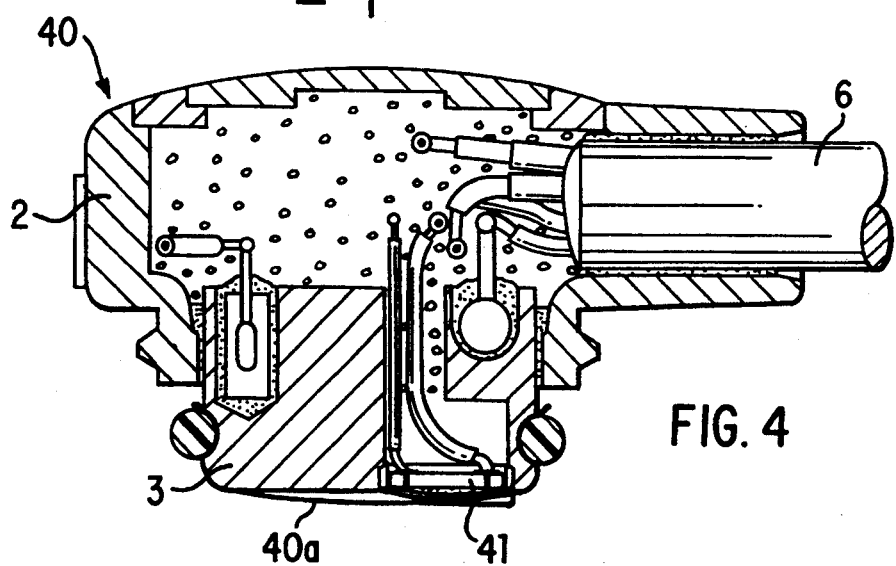
FIG. 4 is a partial cross section of parts of a second embodiment of a sensor according to the invention.
Figures 4A, 4B:
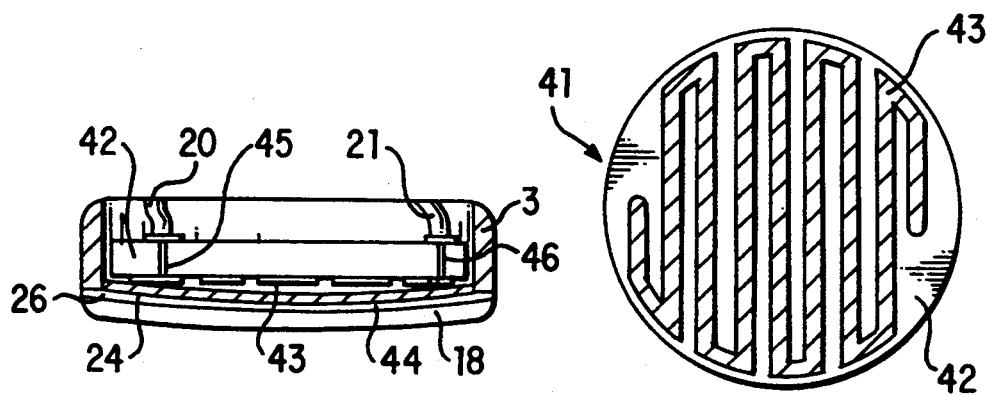
FIG. 4a is a section of FIG. 4 on an enlarged scale.
FIG. 4b is a schematic view of a self-thermostated temperature sensor used in the sensor shown in FIG. 4.

FIG. 4 shows a second embodiment of a sensor 40 according to the invention. This sensor 40 differs only from the above shown sensor 1 in that the thermistor 16 is substituted by another self-thermostating element 41. The element 41 is arranged in the sensor body 3 in a manner similar to the arrangement of the above-mentioned thermistor 16, the element 41 being in good thermal relationship with a delimited surface part (calotte 18) of the sensor measuring surface 40a. The element 41 shown in more detail in FIGS. 4a and 4b comprises an electric insulating ceramic substrate 42, a Pt resistance wire 43 being printed onto one side of the substrate 42. A cover layer 44 of glass is applied onto the Pt wire 43. The ends of the Pt wire 43 are led to the other side of the substrate via bushings 45 and 46 and connected to cables 20 and 21, respectively. In FIG. 4b the element 41 is shown as viewed from the measuring surface 40a, the design of the printed Pt wire 43 appearing clearly. Dependent on the nominal resistance of the Pt wire 43, the design, the thickness and width of the wire 43 may be modified. The side of the element 41 carrying the Pt resistance wire 43 and the glass layer 44 is glued to the silver calotte 18 by means of a heat conductive glue as described above in connection with the thermistor 16. The glass layer 44 may be designed to cover the recess wherein the element 41 is arranged. In this case, the silver calotte 18 may be eliminated as the glass layer 44 will form the delimited part of the measuring surface 40a.

Figure 5:
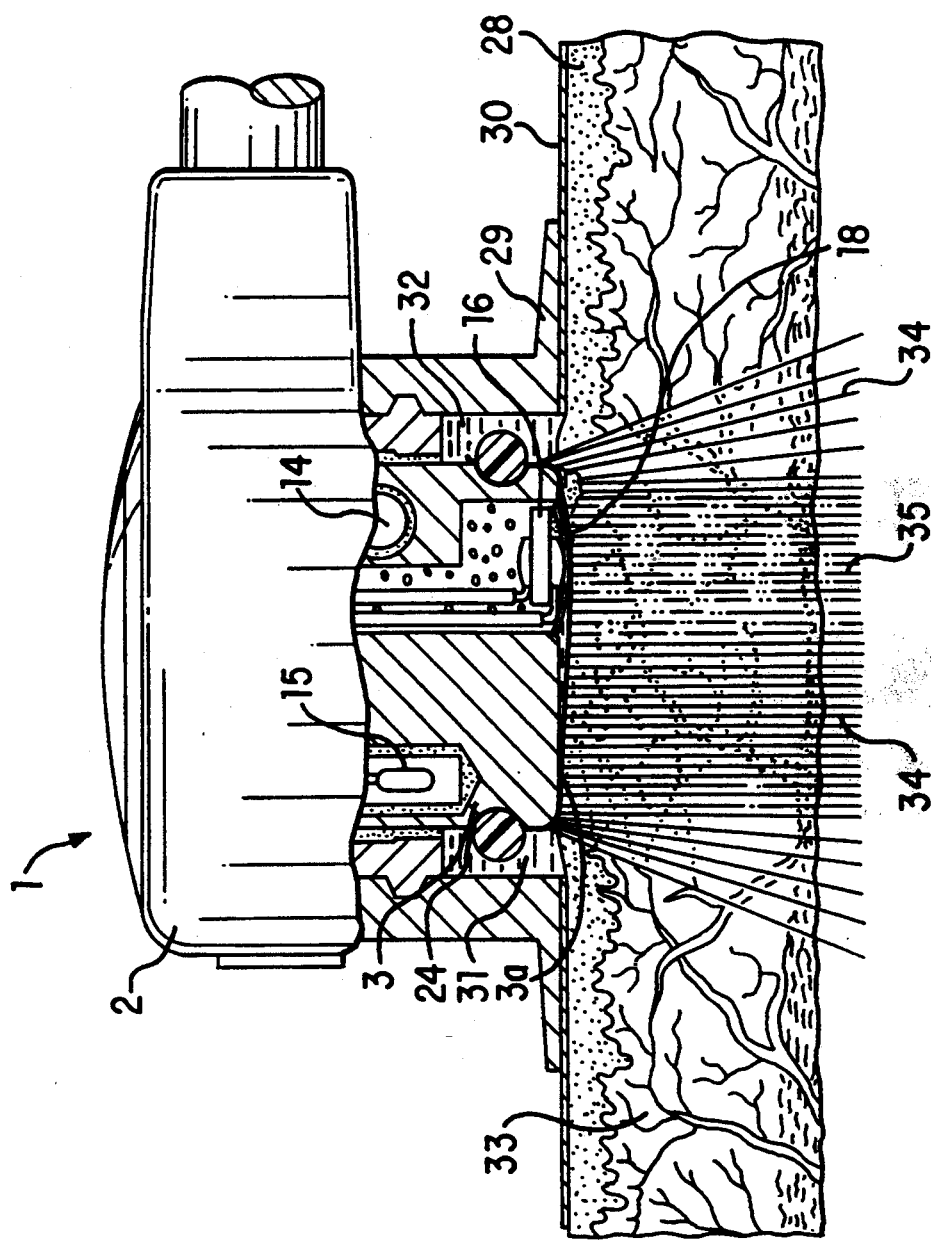
FIG. 5 is a partial cross section of the sensor shown in FIGS. 1–3 applied to a skin surface and including an indication of the heat transfer from the sensor to the skin.

FIG. 5 shows the sensor 1 described in connection with FIGS. 1-3 applied in contact with a skin surface 28. The sensor 1 is secured to the skin 28 by means of an appropriate fixation ring 29 which is mounted on a fixation plaster 30 comprising an adhesive mesh reinforcement. The fixation plaster 30 is adapted for securing the fixation ring 29 to a surface which not necessarily has to be plane, as for example the human skin. The space 31 delimited by the sensor 1, the fixation ring 29 and the skin surface 28, is filled with a contact liquid 32 ensuring a good contact between the skin surface 28 and the membrane 24 stretched across the measuring surface 3a.

When the sensor 1 is to be used for measuring, the sensor 1 is heated merely by means of the heating element 14 until the predetermined measuring temperature for tc measurements of blood gases is registered by the NTC resistor 15 as well as by the thermistor 16. In this manner it is ensured that the sensor body 3 and the thermistor 16 are heated to the same initial temperature and thus that the heat flux between the sensor body 3 and the thermistor 16 is zero. The sensor 1 is calibrated while being heated by the heating element 14 and is then mounted in a fixation ring 20 applied to the selected measuring site on the skin surface 28. After approx. 10-15 min. the conditions required for measuring $CO_2$ and $O_2$ in the tissue is obtained and measuring may be initiated.

During measuring the sensor body 3 is thermostated by means of the heating element 14 and the temperature sensor 15 in order to keep the body 3 and the measuring site at the initial temperature. The thermistor 16 now being thermostated by itself is kept essentially at this temperature as well, however in short pulses of a few seconds, for example 1-4 seconds, the thermistor 16 is heated to a higher temperature appropriate for measuring blood flow. The blood flow measurement proper is performed during said pulse heating. In this way a well-established temperature of the $pCO_2$ and $pO_2$ sensor parts 7 and 8 is obtained, thus obtaining well-established conditions for measuring said parameters and at the same time obtaining appropriate conditions for measuring blood flow. The pulsing short heating of the thermistor 16 does not result in any detectable heating of the sensor 1 and the measuring site beneath the sensor 1. Thereby, the measuring period is not controlled by the temperature for measuring blood flow, but by the temperature for measuring the blood gas parameters $pCO_2$ and $pO_2$. Thus, a measuring period of 4 hours as is usual when using the above-mentioned combined tc sensor of the type E5280 is applicable when using the sensor 1 as well.

When the thermistor 16 and the sensor body 3 are heated to approximately the same temperature, the heat from the sensor body 3 and the thermistor 16, respectively, will radiate through the skin surface 28 into the tissue 33 beneath as depicted by the lines 34 and 35 in FIG. 5. As shown in the figure, heat 34 from the sensor body 3 will heat the skin and the tissue in an area surrounding the silver calotte 18, thus providing a heat shield in the skin surrounding the heat 35 from the thermistor 16. The power supplied to the thermistor 16 during a measurement will thus be supplied as heat to the skin and the tissue right beneath the silver calotte 18 (cf. the lines 35) and not dissipated to other areas of the skin 28 and the tissue 33 or to the remaining surroundings of the sensor 1.

The heat dissipated in the thermistor 16 is absorbed and led away by the blood flowing through the tissue and the power supplied to the thermistor is thus an indication of the blood flow in the tissue located beneath the silver calotte 18. Conversion of dissipated power to a measure of the blood flow is disclosed e.g. in the above-mentioned International Patent Application WO 83/01510 or in Siggaard-Anderson O et al. Model for calculating skin perfusion from heat flux measured with a double heated transcutaneous $pO_2$ electrode. Scand J Clin Lab Invest 1988; 48/189: 21-25. The content of said publications is considered incorporated into the present application by reference to the publications.

In the embodiments disclosed above the systems for measuring the blood flow comprise few components (the thermistor 16, cf. FIGS. 1-3/the thermostated element 41, cf. FIG. 4 and the silver calotte 18). By configuring the systems as shown, a very low thermal mass of said systems is obtained, while at the same time obtaining a large contact surface (the area of the silver calotte 18) between the measuring systems and the skin.

Thus, a large sensitivity and fast response of the measurements are obtained.

By using a combined heating and temperature sensing unit (the thermistor 16/the thermostated elements 41) instead of using two separate units a further advantage is obtained in that fewer supply lines are required to the sensor.

I claim:

1. A sensor for non-invasive in-vivo determination of both an analyte concentration and blood flow, the sensor comprising:
   I. a sensor body comprising:
      a) analyte sensing means comprising an analyte sensor surface for application to a human body in heat-conductive relation therewith for determination of the analyte concentration, the analyte sensor surface having an outer periphery; and
      b) a first thermostating system for establishing and maintaining the sensor body and analyte sensor surface at a first temperature;
   II. blood flow sensing means comprising a blood flow sensor surface located adjacent to the analyte sensor surface and adapted for heat-conductive application to the human body simultaneously with the analyte sensor surface, the blood flow sensor located within the outer periphery of the analyte sensor surface; and
   III. a second thermostating system located within the sensor body in heat-insulated relation therewith and in heat conductive relation with the blood flow sensor surface, the second thermostating system adapted to heat the blood flow sensor surface to a second temperature different from the first temperature for a period of time sufficient to enable determination of the blood flow at the second temperature while not significantly changing the temperature of the analtye sensor surface from the first temperature.

2. The sensor according to claim 1 wherein the analyte sensing means comprises blood gas measuring means.

3. The sensor according to claim 1 wherein:
   the sensor body comprises a recess extending through the analyte sensor surface to the interior of the sensor body;
   the blood flow sensing surface is located in the recess immediately adjacent to the analyte sensor surface; and
   the second thermostating system is located within the recess in the interior of the sensor body immediately adjacent to the blood flow sensor surface.

4. The sensor according to claim 3 wherein the blood flow sensor surface is covered with a layer of a heat-conductive material.

5. The sensor according to claim 3 wherein one or both of the first and second thermostating systems comprises a self-thermostating element.

6. The sensor according to claim 5 wherein the self-thermostating means comprises a thermistor or resistance wire.

7. The sensor according to claim 1 wherein one or both of the first and second thermostating systems comprises a self-thermostating element.

8. The sensor according to claim 1 wherein the blood flow sensing means comprises the second thermostating system.

9. The sensor according to claim 8 wherein the blood flow sensing means comprises a self-thermostating element.

* * * * *